United States Patent [19]

Kuhn

[11] Patent Number: 5,055,044
[45] Date of Patent: Oct. 8, 1991

[54] DENTAL HANDPIECE WITH REMOVABLE HANDPIECE SLEEVE

[75] Inventor: Bernhard Kuhn, Schemmerhofen, Fed. Rep. of Germany

[73] Assignee: Kaltenbach & Voigt GmbH & Co., Biberach/Riss, Fed. Rep. of Germany

[21] Appl. No.: 558,785

[22] Filed: Jul. 26, 1990

[30] Foreign Application Priority Data

Aug. 25, 1989 [DE] Fed. Rep. of Germany ....... 3928211

[51] Int. Cl.$^5$ .............................................. A61C 1/08
[52] U.S. Cl. .................................................... 433/126
[58] Field of Search ........................ 433/126, 127, 128

[56] References Cited

U.S. PATENT DOCUMENTS

| 583,625 | 6/1897 | Lusby et al. | 433/128 X |
| 1,205,553 | 11/1916 | Lyon | 433/126 X |
| 2,376,294 | 5/1945 | Wahlberg | 433/126 |
| 2,376,295 | 5/1945 | Wahlberg | 433/126 |
| 2,876,015 | 3/1959 | Steuer et al. | 433/126 X |
| 3,475,817 | 11/1969 | Loge | 433/126 X |
| 3,631,597 | 1/1972 | Lieb et al. | 433/126 X |

FOREIGN PATENT DOCUMENTS

| 463543 | 3/1927 | Fed. Rep. of Germany | 433/127 |
| 624716 | 5/1933 | Fed. Rep. of Germany | 433/127 |
| 565506 | 12/1930 | Fed. Rep. of Germany | 433/127 |
| 2234321 | 10/1973 | Fed. Rep. of Germany | . |
| 2718750 | 11/1978 | Fed. Rep. of Germany | 433/127 |
| 3402585 | 8/1985 | Fed. Rep. of Germany | 433/126 |

Primary Examiner—Robert P. Swiatek
Assistant Examiner—Nicholas D. Lucchesi
Attorney, Agent, or Firm—Scully, Scott, Murphy & Presser

[57] ABSTRACT

A handpiece with a detachable or removable handpiece sleeve for worktools or dental implements which are releasably inserted with the assistance of a clamping jaw which is rotatable through the intermediary of a drive shaft. The collet is maintained in a clamped position through the action of a spring, wherein the collet has an external conically-tapered end thereof facing towards the implement contacting against a conformingly conically-tapered end of a spindle sleeve facing towards the implement and which is arranged within the handpiece, includes an arresting device. The handpiece sleeve, which is of a single-piece or unitary construction, is retained within an actuating sleeve and is insertable in an axial direction into the actuating sleeve, that in the axial end position the handpiece sleeve is movable through a limited turning or rotational movement into a position in which it is secured against axial movement, and is locked in this position within the actuating sleeve through the intermediary of a latching mechanism thereby producing a handpiece in which there is reduced the danger of potential contamination, the cleaning, care and servicing thereof is rendered easier and, nevertheless, the connection between the handpiece sleeve and the driving and operating components is simplified, so as to thereby render possible an easier assembly and a similarly easy disassembly.

4 Claims, 3 Drawing Sheets

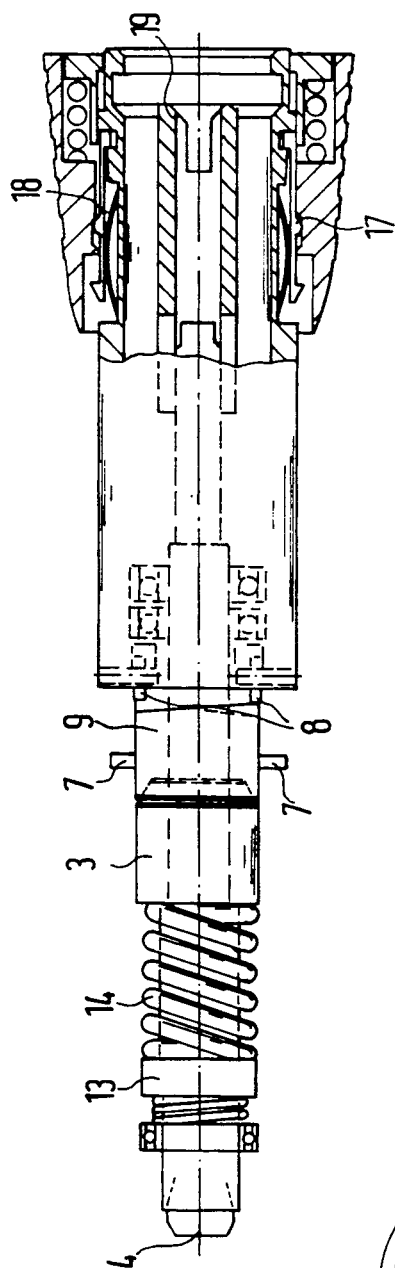
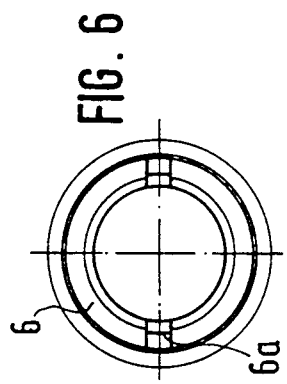
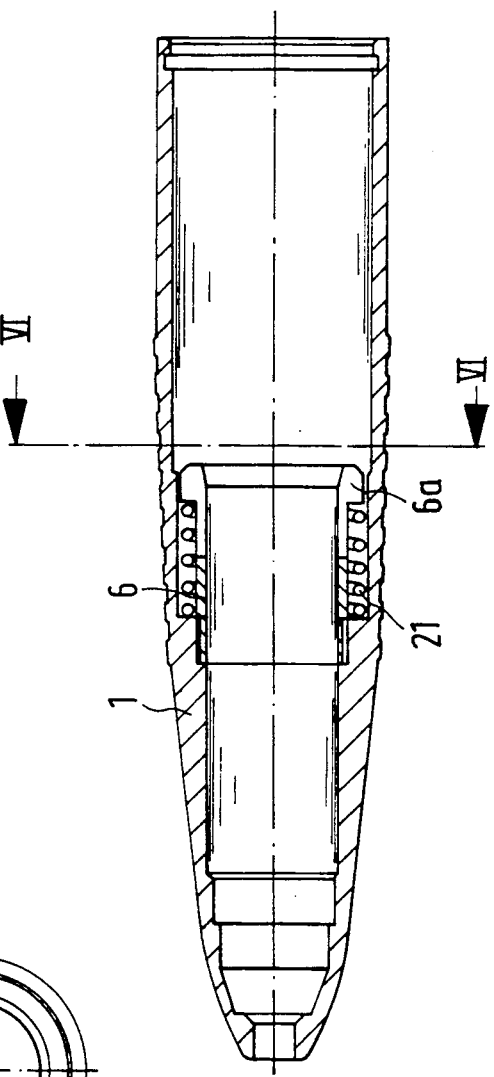

DENTAL HANDPIECE WITH REMOVABLE HANDPIECE SLEEVE

BACKGROUND OF THE INVENTION

1. Field of the Invention

The present invention relates to a handpiece with a detachable or removable handpiece sleeve for worktools or dental implements which are releasably insertable with the assistance of a clamping jaw which is rotatable through the intermediary of a drive shaft, wherein the collet is maintained in a clamped position through the action of a spring, wherein the collet has an external conically-tapered end thereof facing towards the implement contacting against a conformingly conically-tapered end of a spindle sleeve facing towards the implement and which is arranged within the handpiece; includes an arresting device.

2. Discussion of the Prior Art

A handpiece of that type is known from the disclosure of German Laid-Open Patent Appln. 22 34 321. The invention disclosed in that publication is concerned with enhancing the easy handling or action of a specialized threaded sleeve. Hereby, for this purpose, a releasable locking device is provided for at least one end position of the threaded sleeve.

A disadvantage of the above-mentioned known handpiece resides in that the handpiece sleeve is constructed in two separate parts. This creates the formation of a gap which allows for the penetration of impurities or contaminants, such as dust, blood and other undesired materials into the interior of the handpiece containing the sensitive driving components, the clamping device for the dental implement and the mechanism for the release thereof; whose functioning can be adversely influenced to such an extent that the handpiece will prematurely fail or malfunction, and as a result, must be disassembled and cleaned, as well as disinfected. Furthermore, it is also disadvantageous that through a connection between the handpiece sleeve and the functional components which cannot be detached because of the drive conditions, the cleaning, care and servicing is rendered much more difficult.

SUMMARY OF THE INVENTION

Accordingly, the present invention has as an object the provision of a handpiece of the type described herein in which the handpiece sleeve, which is of a single-piece or unitary construction, is retained with an actuating sleeve and is insertable in an axial direction into the actuating sleeve, that in the axial end position the handpiece sleeve is movable through a limited turning or rotational movement into a position in which it is secured against axial movement, in effect, a bayonet-joint, and is locked in this position within the actuating sleeve through the intermediary of latching means thereby producing a handpiece in which there is reduced the danger of potential contamination, the cleaning, care and servicing thereof is rendered easier and, nevertheless, the connection between the handpiece sleeve and the driving and operating components is simplified, so as to thereby render possible an easier assembly and a similarly easy disassembly.

Pursuant to the invention, deviating from the basic type of construction, there is employed the latching or arresting mechanism in order to ensure the positioning of the handpiece sleeve relative to the actuating sleeve.

The advantages which can be ascertained and achieved through the present invention consist of in an avoidance of the penetration or entry of contaminants or impurities of all kinds into the closed, single-piece handpiece sleeve, the simple assembling, the similarly simple disassembling and thereby the cleaning and care as well as servicing, a rapid exchange of handpiece sleeves which may have been contaminated due to other reasons, and finally a simple and rapid exchange of differently structured and configured handpiece sleeves.

Additional features of the invention may also be ascertained as set forth hereinbelow, wherein in particular there is afforded the capability of a simple exchange of the implement in that during the turning of the handpiece sleeve there is turned a rotatable pressure sleeve on which there is provided an inclined or tapered rolling plane along which there roll pressure rollers, as a consequence of which a clamping sleeve is axially displaceable in such a manner that the clamping or tensile action of a spring supported thereon, having on the other hand thereof contacting against an annular shoulder on the spindle sleeve is eliminated so as to cause the collet to be opened and allowing for removal of the implement.

BRIEF DESCRIPTION OF THE DRAWINGS

Further features of the invention may now be more readily ascertained from the following detailed description of exemplary embodiments thereof, taken in conjunction with the accompanying drawings; in which:

FIG. 4 illustrates a longitudinal view, partly in section, of the internal components of the handpiece constructed pursuant to the invention;

FIG. 5 illustrates the end of the handpiece facing towards the implement, with the omission of a number of detail parts; and FIG. 6 illustrates a sectional view perpendicular to the longitudinal axis, taken along line VI—VI in FIG. 5.

DETAILED DESCRIPTION

Figure 1:
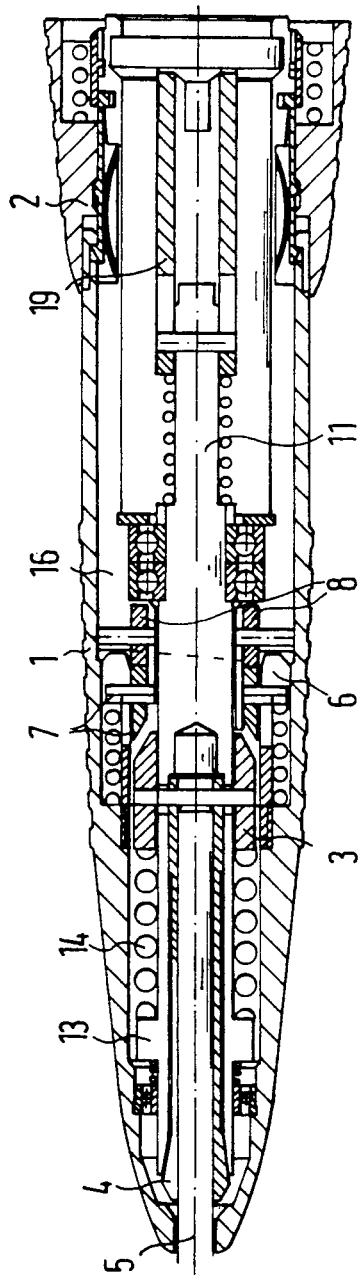
FIG. 1 illustrates a longitudinal sectional view through a handpiece constructed pursuant to the invention.

The handpiece, in its external configuration or construction, consists of a unitarily-constructed handpiece sleeve 1 which is axially inserted into an actuating sleeve 2. Reference numeral 3 designates a clamping sleeve which is connected by means of a cross pin with a spindle sleeve 13, whose end facing towards the dental implement is internally conically tapered. A collet 4, whose end facing towards the implement is conformingly tapered, operates in conjunction with the first-mentioned tapered surface, so as to maintain the worktool or dental implement in a clamped or load-transmissive engagement. Arranged within the collet 4 is an implement shaft 5 which leads to the dental implement (not shown).

Reference numeral 6 identifies a positioning sleeve which includes at least two radially outwardly extending positioning pins 7. Reference numeral 8 identifies pressure rollers which can roll down along a tapered rolling surface or plane 10 on a pressure sleeve 9.

The curved arrow 12 illustrates the direction in which the handpiece sleeve 1 is to be rotated relative to the actuating sleeve 2 in order to release the clamping connection between both sleeves 1, 2.

Formed on the spindle sleeve 13 is an annular shoulder against which a spring 14 supports itself, which spring has the other end thereof contacting against the clamping sleeve 3, and which produces the contacting against each other of the two conically tapered ends of the components 4 and 13 extending towards the dental implement; as a result of which the collet 4 is pressed inwardly against the implement shaft 5, and thereby assures the clampingly load-transmissive or positive restraint of the dental implement; which restraint is so strong that the dental implement in this position cannot be removed towards the front, and will also afford the transmission of the torque from the driving motor to the dental implement.

Figure 3:
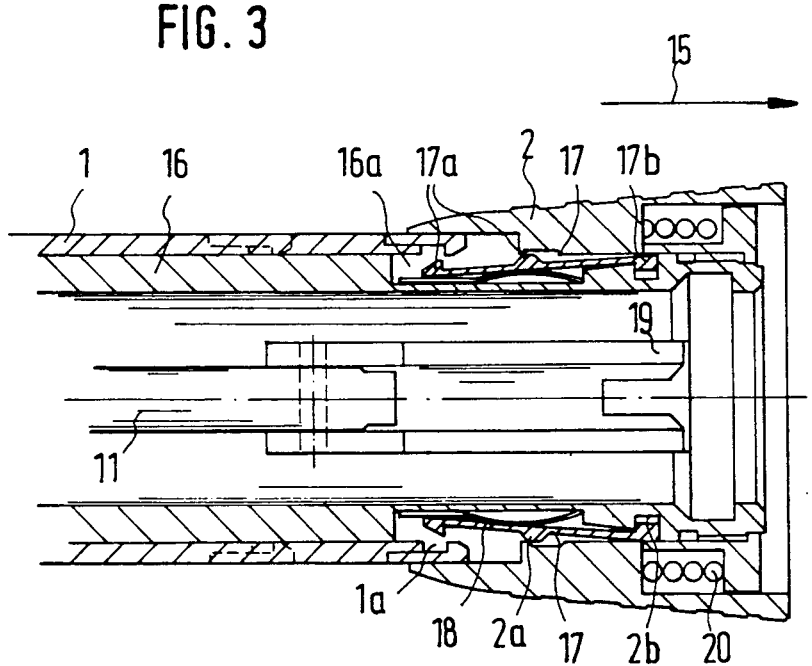
FIG. 3 illustrates an enlarged sectional view through a fragmentary detail.

FIG. 3 illustrates the latching mechanism by means of which there is achieved the arresting or locking together of the two sleeves 1, 2 in their assembled condition. Hereby, the arrow 15 indicates the manner in which the direction of movement of the handpiece sleeve 1 takes place relative to the actuating sleeve 2 during their assembling.

The handpiece sleeve 1 has an inner sleeve 16 insert therein in a close fit. This sleeve 16 is provided at its right-hand end with an external annular groove 16a. Inserted into this groove are the strip-shaped latching elements 17 which are pressed outwardly by means of springs 18, preferably in the form of leaf springs. For the purpose of attaining the arresting action, the handpiece sleeve 1 is provided at its right-hand end with an internal annular groove 1a, into which there engages a projection 17a on the latching element 17 subsequent to the sliding together of the sleeves 1, 2. A second projection 17a on the foregoing element engages into an internal annular groove 2a formed in the actuating sleeve 2. The latter is supported against the inner sleeve 16 by means of a setting or adjusting spring 20.

The latching elements 17 are secured against axial displacement, in that internal or inward projections 17b engage into an outer annular groove formed in the inner sleeve 16. The projections are secured by the actuation sleeve 2 against their falling out, inasmuch as the inner wall of the actuating sleeve 2 encompasses the inner sleeve 16.

Located on the shaft 11, which is positioned to extend coaxially with the implement shaft 5, is a follower 19 serving as a coupling element for effectuating the connection with the shaft of a driving motor (not shown).

From FIG. 5 of the drawings there can be ascertained the positioning sleeve 6, which incorporates at least two axial or longitudinal slots 6a, in which there engage the positioning pins 7 of the pressure sleeve 9 so as to be axially displaceable. The positioning sleeve 6 is supported against the handpiece sleeve 1 through the provision of a spring 21.

FIG. 3 illustrates the manner in which the handpiece sleeve 1 is inserted into the actuating sleeve 2 in accordance with the inventive concept. Thereby, the former is inserted into the latter and axially displaced in the direction of arrow 15. As a result thereof, the right-hand end of the handpiece sleeve 11 slides with a groove (not shown) formed therein past the forward projection 17a on the latching element 17, until this projection engages under the biasing pressure of its spring 18 into the annular groove 1a in the handpiece sleeve 1. Simultaneously, the other projection 17a engages into the annular groove 2a in the actuating sleeve 2. Thereafter, the handpiece sleeve 1 is rotated relative to the actuating sleeve 2 opposite the turning direction 12 by a limited amount. This has as a consequence that the forward projection 17a on the latching element 17 exits from the region of the longitudinal groove and, under a pull exerted opposite the direction 15, seats itself behind the right-hand end of the annular groove 1a and thereby counteracts or opposes a tensile force of a load-transmissive contact. Thereby, in this position, the two sleeves are secured by a bayonet-joint against any axially directed separating forces.

Figure 2:
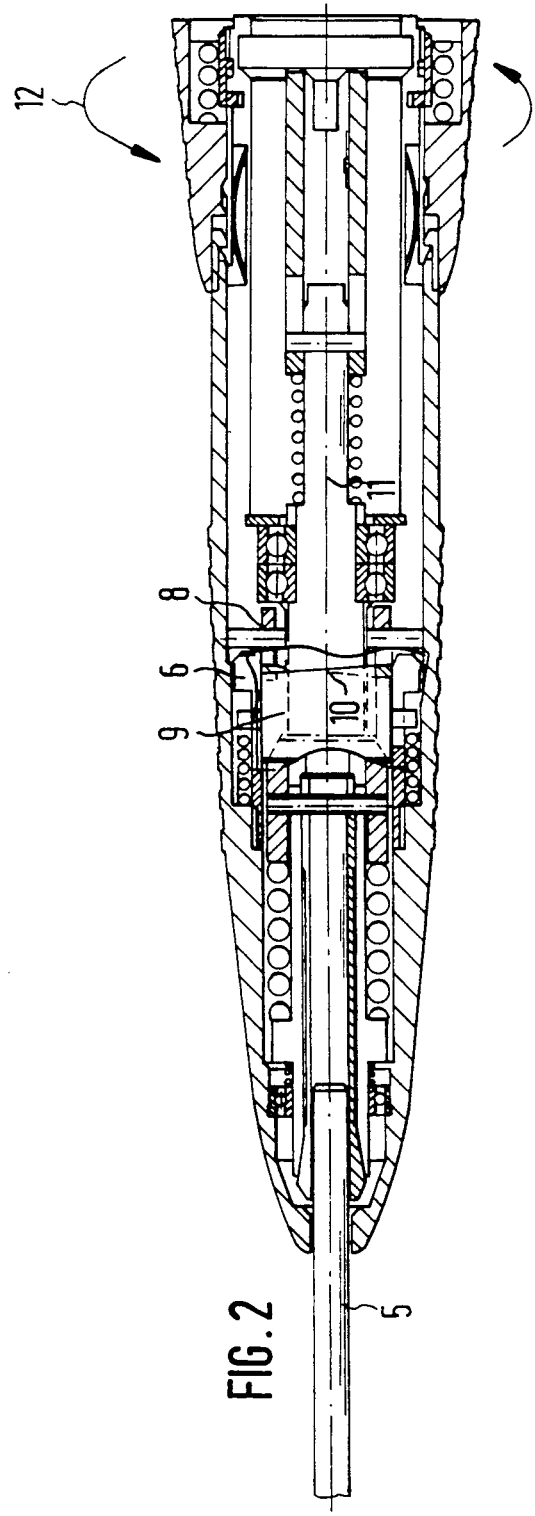
FIG. 2 illustrates a longitudinal sectional view similar to FIG. 1, in which an internal detail is shown in plan view.

In order to loosen or release this connection, the handpiece sleeve 1 is thereafter rotated bayonet-like relative to the actuating sleeve 2 in the context of the arrow 12 (FIG. 2). Subsequently, the two sleeves 1, 2 can be separated from each other opposite the direction of arrow 15.

During turning or rotation, because of the rolling of the pressure rollers 8 along the tapered rolling plane 10 on the pressure sleeve 9, there is concurrently eliminated the force of the spring 14, so that the clamping action releases between the conical surfaces of the components 11 and 13. As a result thereof, the dental implement or worktool has been freed from the load-transmissive connection, and can be forwardly withdrawn from the handpiece sleeve 1, as is indicated in FIG. 2.

What is claimed is:

1. A dental handpiece including a removable handpiece sleeve of unitary construction for dental implements which are releasably insertable therein through the intermediary of a collet which is rotatable by a drive shaft; a spring for maintaining said collet in a clamped position, said collet having an external conically-tapered end towards a retained dental implement and contacting a correspondingly conically-tapered end of a spindle sleeve extending towards the dental implement, said spindle sleeve being arranged within the handpiece cooperating with said first-mentioned tapered end and including a latching arrangement between said sleeves, said handpiece sleeve being insertable in an axial direction into and retained in an actuating sleeve, in the inserted axial position said handpiece sleeve through a limited rotational movement being movable into a position secured against axial movement; and latching means for arresting said handpiece sleeve in said actuating sleeve in this position; said latching means comprises strip-shaped latching elements including projections engaging into, respectively, an internal annular groove formed in the handpiece sleeve and in the actuating sleeve; and spring means comprising a leaf spring, imparting an outwardly directed pressure to said latching elements to provide said engaging action, said spring means being inserted into an external annular groove formed in an inner sleeve which is arranged within the handpiece sleeve.

2. A handpiece as claimed in claim 1, wherein the latching action of said latching means is releasable responsible to a limited turning of said handpiece sleeve relative to said actuating sleeve opposite said first-mentioned limited rotational movement, so as to enable an axial separation of said handpiece sleeve from said actuating sleeve.

3. A handpiece as claimed in claim 1, wherein the inner sleeve extends into the interior of the actuating sleeve in the assembled condition therewith, and said inner sleeve includes an external annular groove; internal projections on said latching elements engaging into said external annular groove and being retained in said groove by an inner wall of the actuating sleeve.

4. A handpiece as claimed in claim 1, wherein a rotatable pressure sleeve is rotated responsive to said rotational movement of said handpiece sleeve; a tapered rolling plane on the surface of said pressure sleeve; pressure rollers rollable along said rolling plane to cause axial displacement of a clamping sleeve which is connected to said pressure sleeve so as to eliminate the clamping action of the spring which is supported thereon, said spring having an opposite end thereof contacting against an annular shoulder on the spindle sleeve to thereby open the collet and enabling withdrawal of the dental implement.

* * * * *